US008807138B2

(12) United States Patent
Byers et al.

(10) Patent No.: US 8,807,138 B2
(45) Date of Patent: Aug. 19, 2014

(54) SURGICAL DRAPE AND METHOD PROVIDING A STERILE SURFACE THEREWITH

(75) Inventors: Terry M. Byers, Flushing, MI (US); Samba Toure, Grand Blanc, MI (US); Michael W. Czop, Fenton, MI (US); Richard A. Weaver, Linden, MI (US)

(73) Assignee: Contour Fabricators, Inc., Fenton, MI (US)

( * ) Notice: Subject to any disclaimer, the term of this patent is extended or adjusted under 35 U.S.C. 154(b) by 403 days.

(21) Appl. No.: 12/820,562

(22) Filed: Jun. 22, 2010

(65) Prior Publication Data

US 2010/0319713 A1 Dec. 23, 2010

Related U.S. Application Data

(60) Provisional application No. 61/269,235, filed on Jun. 22, 2009.

(51) Int. Cl.
*A61B 19/12* (2006.01)
*A61B 19/08* (2006.01)

(52) U.S. Cl.
USPC .......................... 128/849; 128/853; 128/856

(58) Field of Classification Search
USPC ............ 128/849–855, 856; 250/515.1, 517.1, 250/519.1; 378/204
See application file for complete search history.

(56) References Cited

U.S. PATENT DOCUMENTS

| 4,350,246 | A | | 9/1982 | Mayer |
| 5,417,225 | A | | 5/1995 | Rubenstein et al. |
| 5,433,221 | A | * | 7/1995 | Adair ........................... 128/849 |
| 5,523,581 | A | * | 6/1996 | Cadwalader ............... 250/519.1 |
| 5,676,159 | A | * | 10/1997 | Navis ........................... 128/846 |
| 6,278,125 | B1 | * | 8/2001 | Belek ........................ 250/519.1 |
| 7,604,007 | B1 | * | 10/2009 | Wooley ........................ 128/849 |
| 2002/0109107 | A1 | | 8/2002 | Goldstein |
| 2003/0205233 | A1 | | 11/2003 | Aboul-Hosn et al. |

FOREIGN PATENT DOCUMENTS

WO     9638096     12/1996

* cited by examiner

*Primary Examiner* — Patricia Bianco
*Assistant Examiner* — Camtu Nguyen
(74) *Attorney, Agent, or Firm* — John D. Wright; Dickinson Wright PLLC

(57) ABSTRACT

A surgical drape and method of providing a sterile surface therewith is provided. The drape is configured to cover an upper portion of a radiation shield and includes a flexible wall providing a cavity sized to receive the upper portion of the radiation shield. The flexible wall has a rear wall portion configured to cover at least in part a rear portion of the radiation shield and a front wall portion configured to cover a front portion of the radiation shield. The front wall portion extends to an upper front free edge and the rear wall portion extends to an upper rear free edge. At least one fastener is attached to at least one of the front and rear wall portions adjacent respective ones of the upper front free edge and rear free edge. The fastener is configured to releasably fix the front and rear walls to the radiation shield.

20 Claims, 14 Drawing Sheets

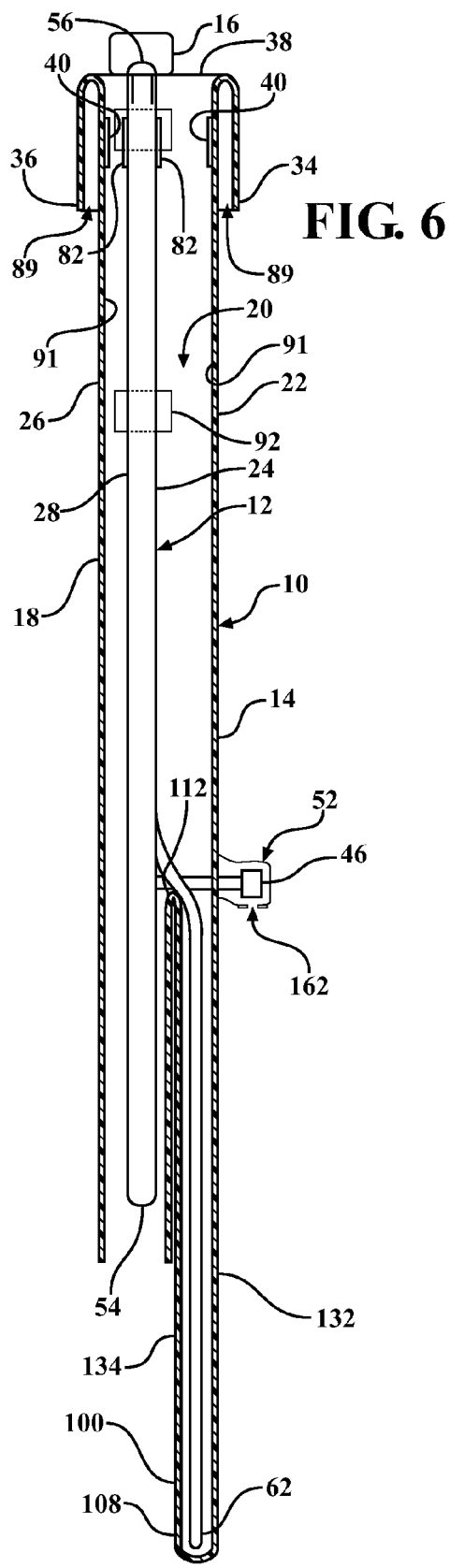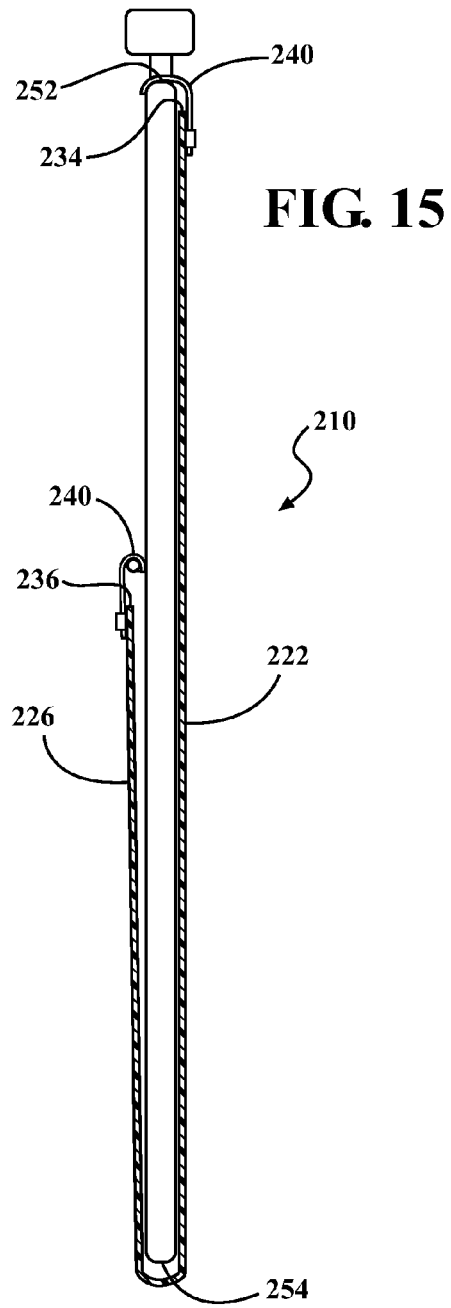

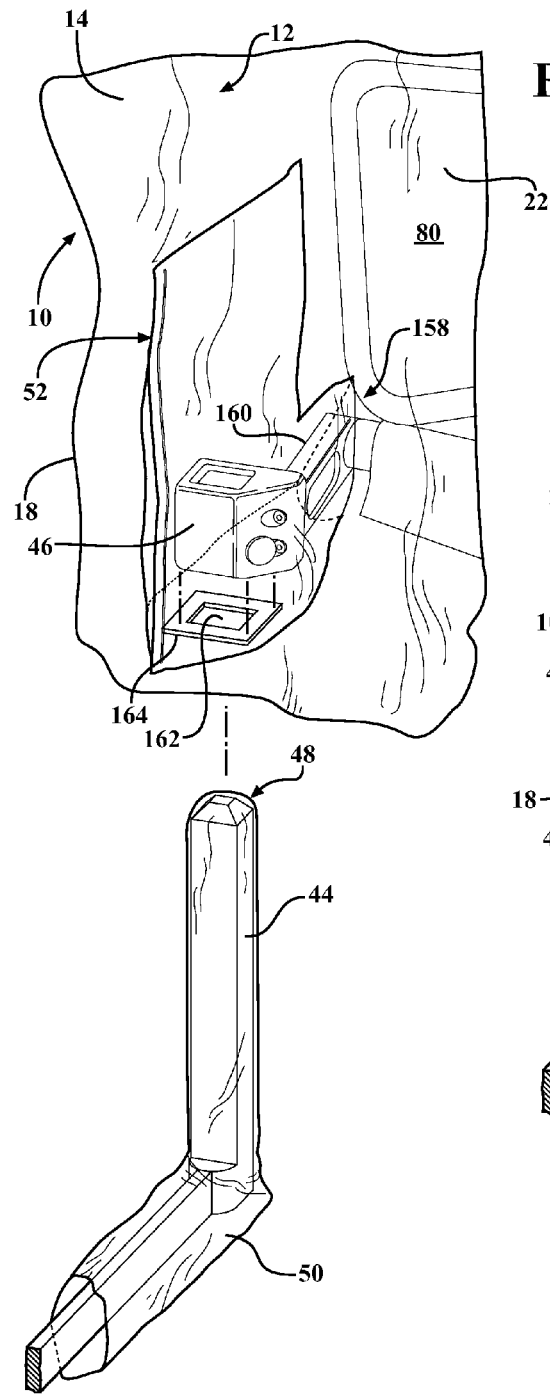
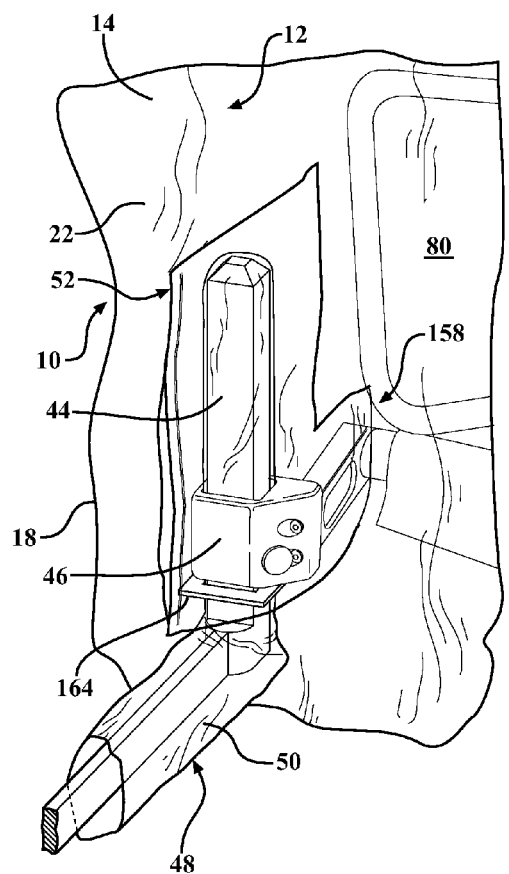
FIG. 11
FIG. 12

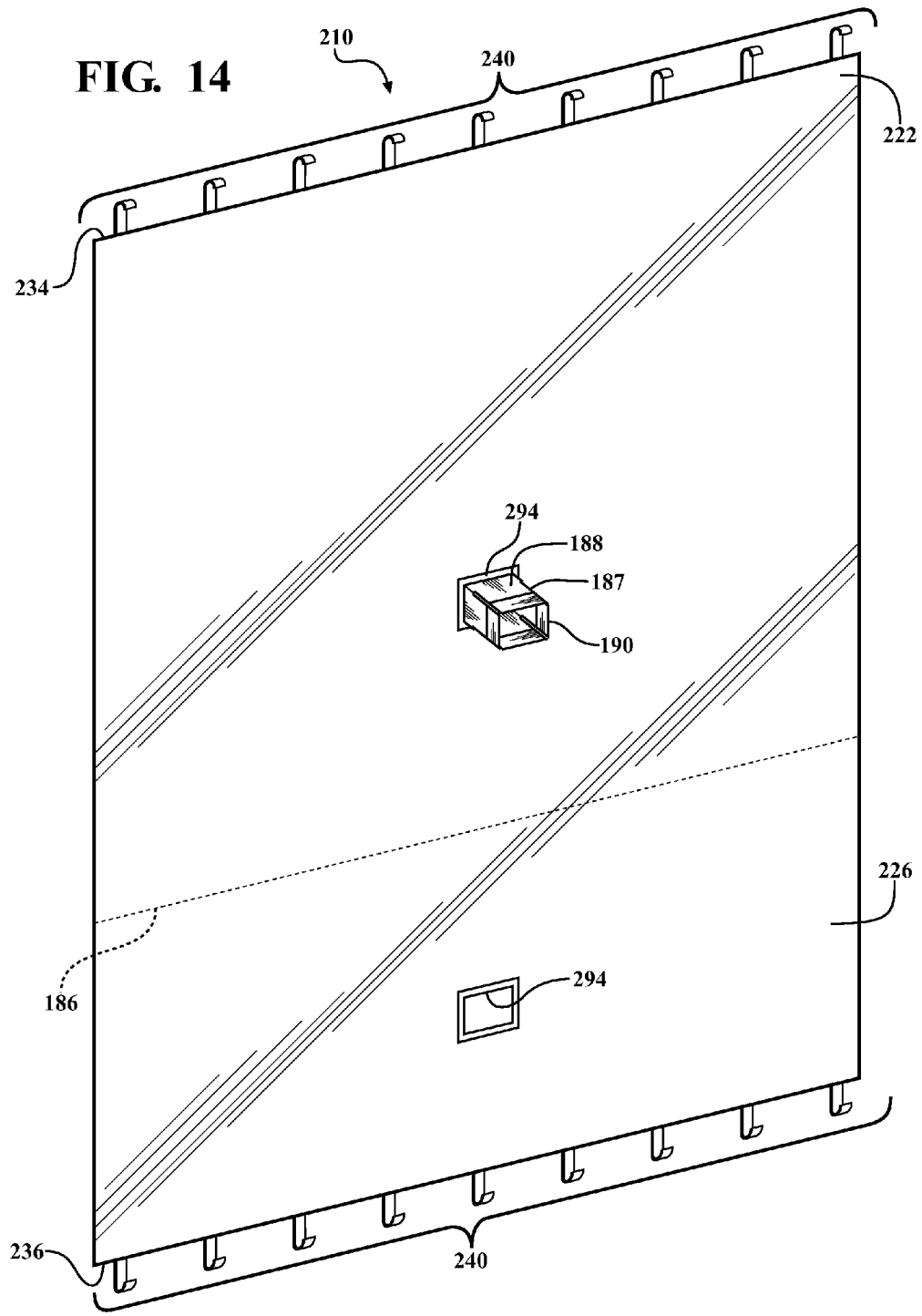

SURGICAL DRAPE AND METHOD PROVIDING A STERILE SURFACE THEREWITH

CROSS-REFERENCE TO RELATED APPLICATIONS

This application claims the benefit of U.S. Provisional Application Ser. No. 61/269,235, filed Jun. 22, 2009, which is incorporated herein by reference in its entirety.

BACKGROUND OF THE INVENTION

1. Technical Field

This invention relates generally to surgical drapes, and more particularly to disposable surgical drapes used to cover surgical equipment to maintain sterility in a surgical theatre.

2. Related Art

The need to provide a sterile environment in a surgical theatre is directly associated with the known risk of infection that can be caused by bacteria, such as from a person or surgical equipment, in the surgical theatre. As such, it is known that in order to minimize the risk of infection during a surgical procedure, it is necessary to prevent the transfer of bacteria, such as via airborne lint or dust particles, fluids, or otherwise, within the surgical theatre.

Surgical drapes are commonly used during surgical procedures to prevent the transfer of bacteria, thereby maintaining sterility in the surgical theatre. The surgical drapes cover surgical equipment to present an external sterile surface about the equipment. By covering the underlying surgical equipment, not only is an external sterile surface quickly provided, but any bacteria on the underlying equipment prevented from being transferred throughout the surgical theatre, and the underlying equipment is also protected during the surgical procedure. Without surgical drapes, it becomes necessary to sterilize the surgical equipment thoroughly before and after each surgical procedure, which is labor intensive consuming a great deal of time, and thus, costly.

A wide variety of surgical drapes have been developed to improve sterility at the operative site. During some surgical procedures, multiple surgical drapes are employed to reduce the potential for infection. For example, during radiological surgical procedures using a radiation shield deployed over a patient's torso, it is known to deploy multiple surgical drapes about the patient and the radiological shield, including a drape deployed about the patient's head/neck region in order to prevent bacteria from being transferred from an anterior, non-sterile side of the radiation shield to a posterior, sterile side of the radiation shield to the location of the surgical procedure. This is typically the case when surgical support staff, such as a perfusionist, is positioned on the non-sterile, anterior side of the radiological shield while the surgical team performs surgery on the sterile, posterior side of the radiological shield.

Of the surgical drapes known, there are two types. One type is reusable, while the other is disposable. Of course, reusable drapes require re-sterilization after each use, and of course, the sterility must be maintained after re-sterilizing and prior to future use. This requires having sterilization equipment available; is labor intensive, and thus, costly. In addition, having to re-sterilize the drapes introduces an increased possibility that the reusable drape either not becoming completely re-sterilized, or that the re-sterilized drape becomes contaminated prior to future use, such as via improper repackaging.

The known disposable drapes, while doing away with the concern of re-sterilization and offering an ability to provide a sterile surface desired, commonly require separate, multiple drapes to cover all the surfaces requiring draping. In addition, the known disposable surgical drapes are challenging to deploy, both generally speaking and in proper fashion to maintain sterility, and non-conforming to the underlying surgical equipment upon being deployed. As such, portions of the drapes are commonly baggy, thus, can get in the way of the transfer of surgical instruments between the anterior and posterior sides of the radiological shield during surgery.

SUMMARY OF THE INVENTION

A surgical drape configured to cover an upper portion of a suspended radiation shield includes a flexible wall providing a cavity sized to receive the upper portion of the radiation shield therein. The flexible wall has a rear wall portion configured to cover at least in part a rear portion of the radiation shield and a front wall portion configured to cover a front portion of the radiation shield. The front wall portion extends to an upper front free edge and the rear wall portion extends to an upper rear free edge. The upper front and rear free edges provide the wall with an open upper end. At least one fastener is attached to at least one of the front and rear wall portions adjacent respective ones of the upper front free edge and rear free edge. The fastener is configured to releasably fix the front and rear walls to the radiation shield.

In accordance with another aspect of the invention, a method of providing a sterile surface on a suspended radiation shield extending vertically between a laterally extending lowermost edge and a laterally extending uppermost edge is provided. The method includes providing a folded, sterile flexible drape having a rear wall portion configured to cover at least in part a rear portion of the radiation shield and a front wall portion configured to cover a front portion of the radiation shield. The front wall portion is configured to extend to an upper front free edge and the rear wall portion to extend to an upper rear free edge with at least one fastener attached adjacent to at least one of the front and rear free edges. The method further includes positioning the lowermost edge of the radiation shield in a sterile region above a non-sterile field. Then, covering the front portion of the radiation shield with the front wall portion of the drape and covering at least a portion of the rear portion of the radiation shield with the rear wall portion of the drape. And further, releasably attaching the upper front free edge and the upper rear free edge to the radiation shield assembly.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

FIG. 6 illustrates a cross-sectional view taken generally along the line 6-6 of FIG. 5;

FIG. 11 illustrates a pouch of the disposable sterile drape with a receptacle disposed therein, with the receptacle being positioned for receipt of a locating post therein;

FIG. 12 illustrates the locating post received in the receptacle;

FIG. 14 illustrates a perspective view of the disposable sterile drape of FIG. 13; and FIG. 15 illustrates a cross-sectional view of the disposable sterile drape of FIG. 13 shown disposed about the radiation shield.

DETAILED DESCRIPTION OF PRESENTLY PREFERRED EMBODIMENTS

Figure 1:
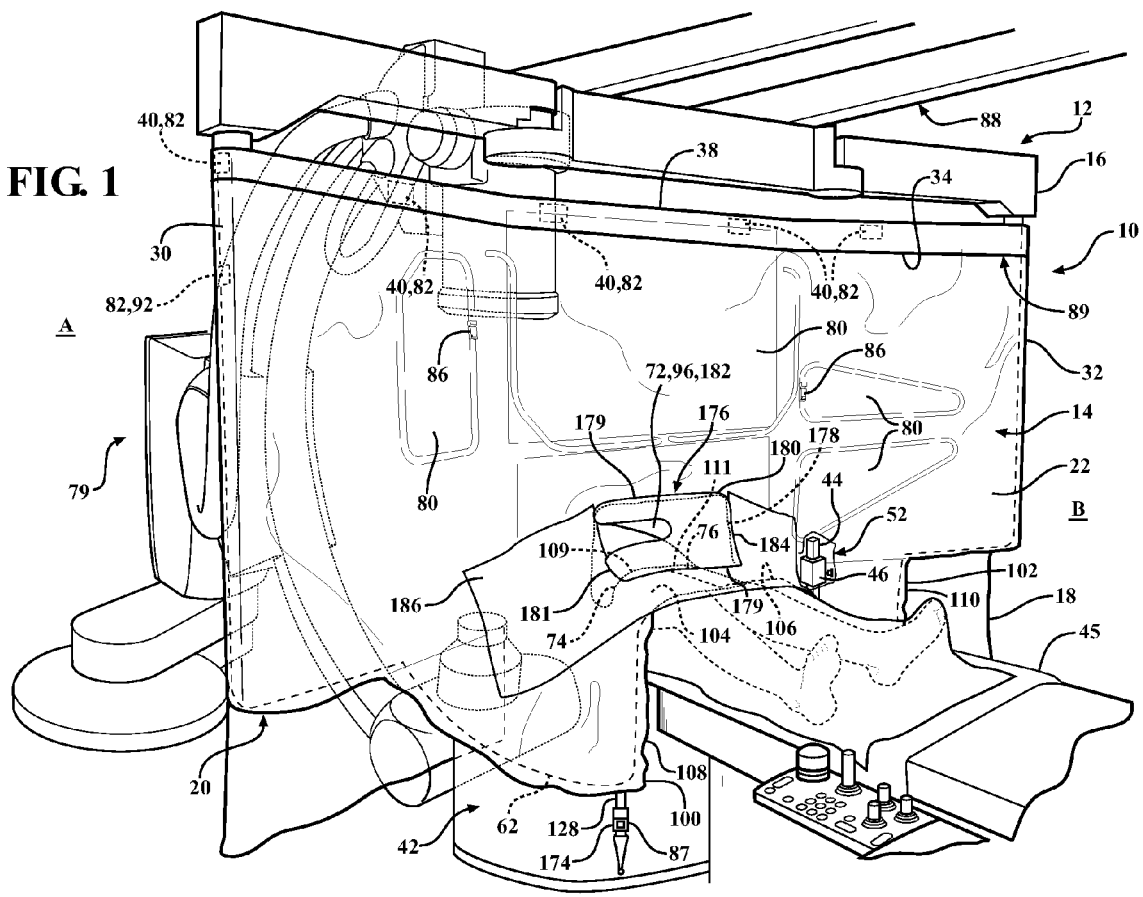
FIG. 1 illustrates a perspective front view of a disposable sterile drape disposed about a radiation shield in accordance with one aspect of the invention.
Figure 1A:
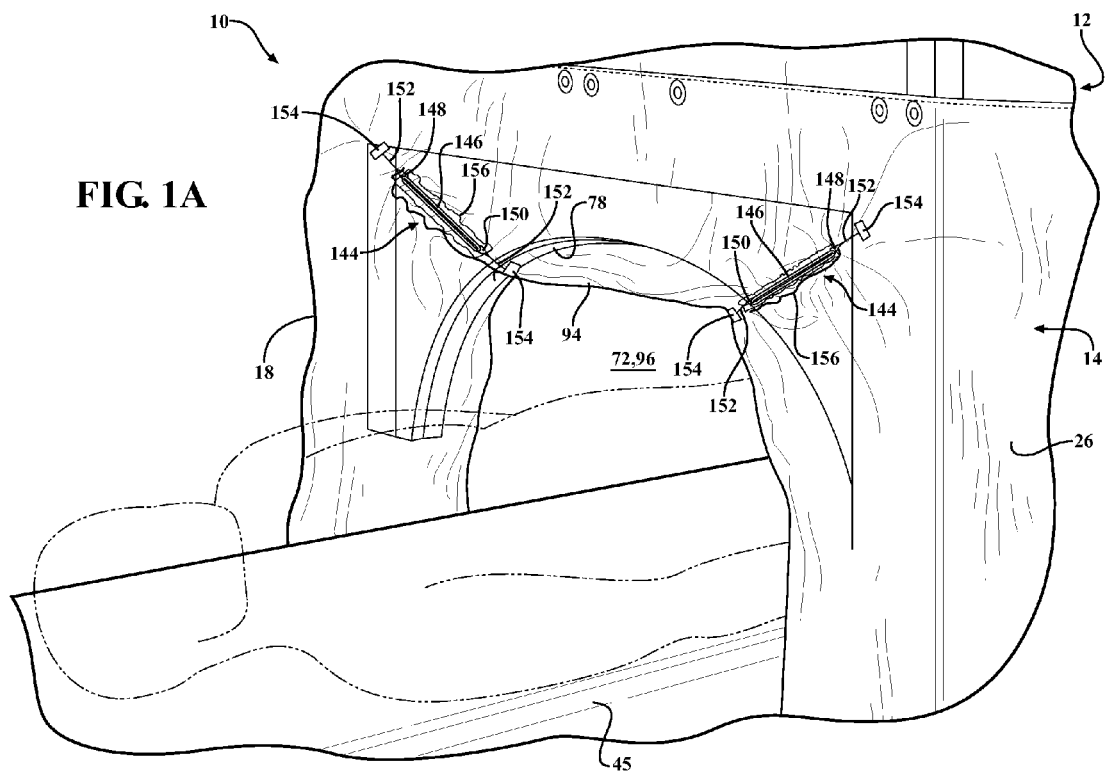
FIG. 1A illustrates a partial perspective rear view of the disposable sterile drape and radiation shield of FIG. 1.
Figure 2:
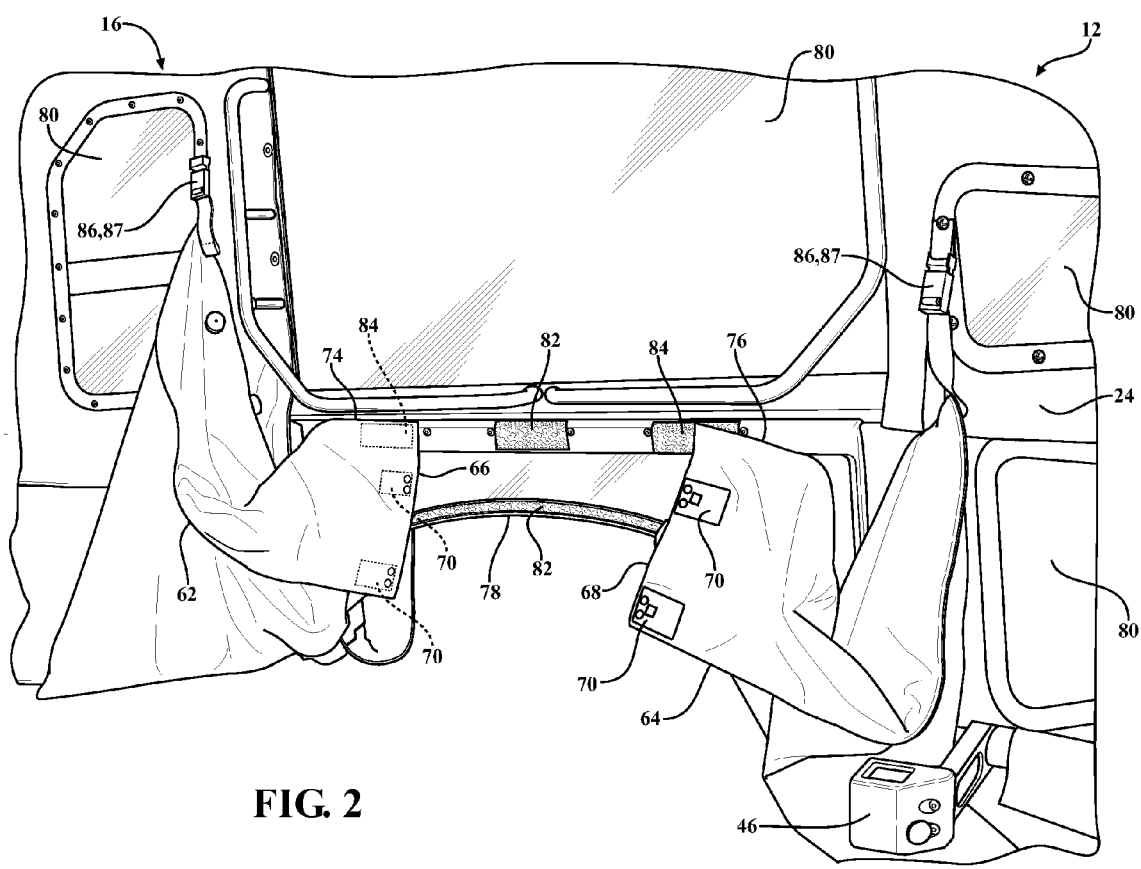
FIG. 2 illustrates a partial front perspective view of the radiation shield of FIG. 1.
Figure 3:
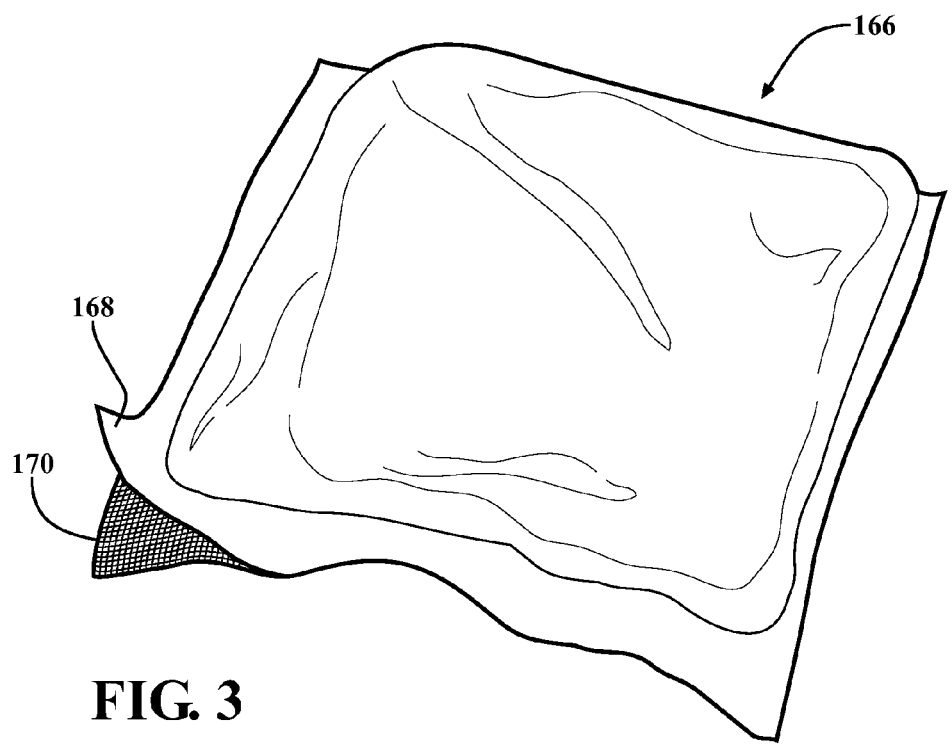
FIG. 3 illustrates the disposable sterile drape of FIG. 1 shown folded in a sterile package.

Referring in more detail to the drawings, FIG. 1 illustrates a disposable sterile surgical drape, referred to hereafter as drape 10, constructed in accordance with one aspect of the invention, with the drape 10 shown disposed about and enclosing a radiation shield assembly, referred to hereafter as radiation shield 12, such as a lead drape, to provide an outer sterile surface 14 about an upper portion 16 of the radiation shield 12. The drape 10 has a flexible, tear and puncture-resistant wall 18 substantially bounding an inner tubular cavity 20, wherein the cavity 20 is sized to receive the upper portion 16 of the radiation shield 12 therein. The flexible wall 18 has a front wall portion 22 configured to cover a front portion 24 of the radiation shield upper portion 16 and a rear wall portion 26 configured to cover a rear portion 28 of the radiation shield upper portion 16. The front and rear wall portions 22, 26 are joined to one another along opposite side edges 30, 32, such as via a weld seam, for example. The front wall portion 22 extends to an upper front free edge 34 and the rear wall portion 26 extends to an upper rear free edge 36. The upper front and rear free edges 34, 36 provide the wall 18 with an open upper end 38. At least one fastener, and shown here as a plurality of fasteners 40 are attached to at least one of the front and rear wall portions 22, 26 adjacent respective ones of the upper front free edge and rear free edge 34, 36. The fasteners 40 are configured to releasably fix the front and rear wall portions 22, 26 to the radiation shield upper portion 16. As such, the drape 10 provides an easy, quick and economical way in which to provide the sterile outer surface 14 about the radiation shield upper portion 16, with the drape 10 being readily removable from the upper portion 16 for disposal after use.

The radiation shield 12 typically includes a lower portion 42 configured to rest on a floor surface and to support the upper portion 16 in use. To facilitate locating the upper portion 16 on the lower portion 42, an upstanding locating post 44 that is generally L-shaped (FIGS. 1, 11 and 12) is provided, and is attached to a frame of a patient table 45. The locating post 44 is sized for close receipt within a receptacle 46 of the radiation shield upper portion 16. When the receptacle 46 is lowered over the post 44, the upper portion 16 is brought into mating abutment with the lower portion 42, whereupon the upper and lower portions 16, 42 are assured of being properly mated and attached to one another.

As shown in FIGS. 11 and 12, a sterile sleeve 48 is provided to cover the post 44, whereby the sleeve 48 provides a sterile outer surface 50 about the post 44. As such, the risk of bacteria on the post 44 causing infection is minimized. The sleeve 48, prior to being disposed on the post 44, is everted in reverse folded fashion on itself so as to reduce its full length by about ½. With the sleeve 48 in its reversed folded state, a pocket of the sleeve 48 is disposed over the post 44, with an upstanding portion of the L-shaped post 44 being covered, and then the sleeve 48 is unfolded in sock-like fashion over the remaining horizontal portion of the L-shaped post 44 whereupon as the sleeve 48 unfolds, the sterile outer surface 50 is revealed on both the upstanding portion and on the horizontal portion of the post 44. Accordingly, upon being completely disposed and unfolded on the post 44, the complete sterile surface 50 of the sleeve 48 faces outwardly for receipt in the receptacle 46. Also shown in FIGS. 1, 5, 11 and 12, is a sterile pouch 52 of the drape 10 that is configured to receive the receptacle 46 prior to receiving the post 44, which is discussed further below.

Figure 7:
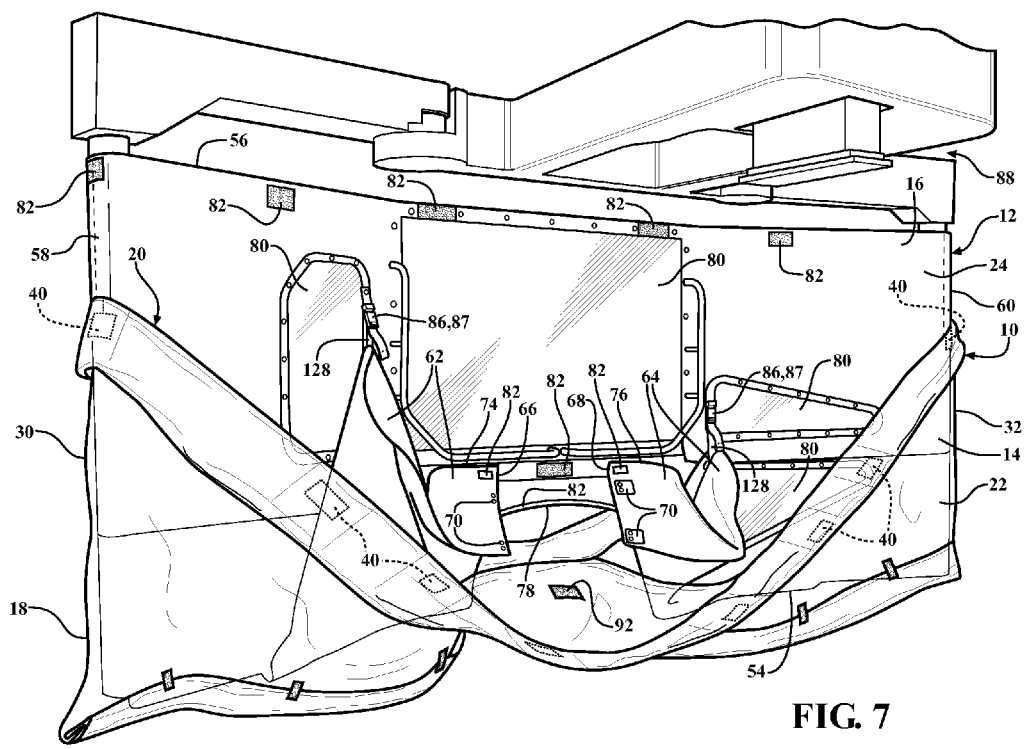
FIG. 7 illustrates the disposable sterile drape in a partially assembled state on the radiation shield.
Figure 8:
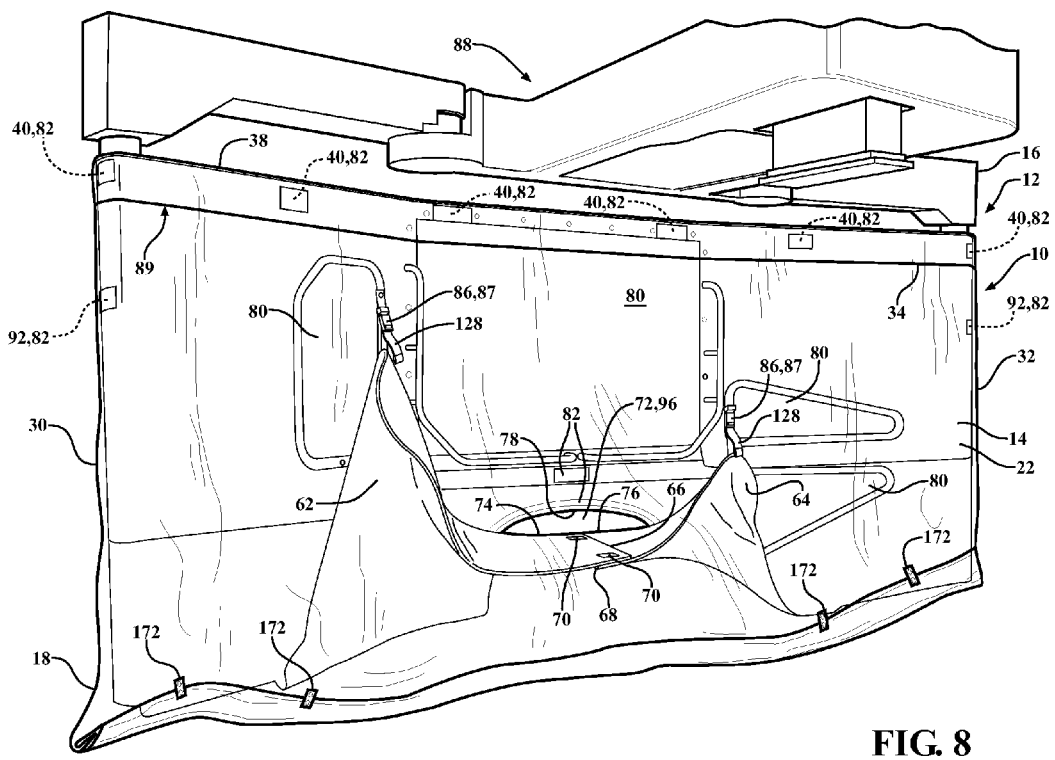
FIG. 8 illustrates the disposable sterile drape fully disposed over the radiation shield and releasably attached thereto.

As shown in FIG. 7, the upper portion 16 of the radiation shield 12 has a laterally extending lowermost end 54 and a laterally extending uppermost end 56 with laterally spaced sides 58, 60 extending vertically therebetween. Spaced laterally inwardly from the sides 58, 60 are a pair of skirts 62, 64 that depend from the lowermost end 54. The skirts 62, 64 are generally L-shaped in mirrored relation with one another across a midpoint of the shield 12, wherein respective ends 66, 68 of the skirts 62, 64 extend laterally to overlap one another during use. To facilitate maintaining the ends 66, 68 in their overlapped relation during use, the ends have fasteners configured to releasably fix the ends 66, 68 to one another, wherein the fasteners in one presently preferred embodiment include magnets 70. Upon the ends 66, 68 being fastened to one another, an enclosed fenestration 72 is formed by inner peripheral edges 74, 76 of the skirts 62, 64 and an upper, arcuate edge 78 arcing above and between the skirts 62, 64.

So that persons on one side (A) of the radiation shield 12, such as the side having radiation emitting imaging equipment, such as a C-arm x-ray emitter 79, for example, can see persons on the other side (B) of the radiation shield 12, at least one transparent window, and shown here as a plurality of transparent windows 80 are provided in the radiation shield 12. The drape 10 does not interfere with the ability to see through the windows 80 because the drape 10, in the embodiment shown, is constructed of a transparent, flexible, tear and puncture-resistant plastic material, such as the type of plastic typically used for surgical drapes, e.g., polyurethane film, polyethylene, polyvinylchloride, thermoplastic olefins, polypropylene, and copolymers of propylene and polyethylene, typically having a thickness between 0.5-3.0 mils, by way of example and without limitation. Accordingly, upon deploying the drape 10, the windows 80 provide viewing areas from one side of the radiation shield 12 to the other. It should be recognized that materials could be used, such as disposable woven or non-woven materials, for example, in lieu of or in combination with plastic materials.

To facilitate attaching the drape 10 to the radiation shield 12, the radiation shield 12 has at least one, and shown here as a plurality of fasteners 82 that correspond in number and mirrored location for attachment with the fasteners 40 on the drape 12. One presently preferred type of fastener mechanism for the fasteners 40, 82 includes hooks and loops, i.e. Velcro®, by way of example and without limitation. A pair of fasteners 82 are located on the opposite sides 58, 60 about midway between the lowermost and uppermost ends 54, 56, while a plurality of fasteners 82 are located adjacent the uppermost end 56 on both the front portion 24 and the rear portion 28. In addition, an elongate fastener 82 is located along the arcuate edge 78 and an additional fastener 82 is located centrally above the arcuate edge 78. It should be recognized that additional fasteners can be deployed, if desired. Further yet, to facilitate maintaining the skirts 62, 64 in a pre-deployed, retracted position, a pair of fasteners 84 are located in laterally spaced relation to the centrally located fastener 82 above the arcuate edge 78. To further assist in retracting the skirts 62, 64 in their pre-deployed position, a pair of fasteners, shown as spring clip receptacles 86, by way of example and without limitation, are located upwardly from the arcuate edge 78 on opposite sides thereof and a pair of mating fasteners 87 are attached to ends of the skirts 62, 64. When the skirts 62, 64 are retracted and the clips 87 fastened to the spring clip receptacles 86, assembly of the drape 10 to the radiation shield 12 is facilitated, wherein the clips 87 of the skirts 62, 64 are selectively detached from the receptacles 86 and allowed to naturally hang downwardly during assembly of the drape 10, discussed further below.

The upper portion 16 of the radiation shield 12 is suspended from its uppermost end 56 and as such, the lowermost end 54 is free. The suspension is provided by an overhead trolley system 88 that allows complete, 3-dimensional movement. Thus, the upper portion 16 of the radiation shield 12 can be translated, raised and lowered and pivoted, as desired, to manipulated the upper portion 16 from a stored location, generally in which the drape 10 is assembled, to the in-use position. In the in-use position, the upper portion 16 is attached to the lower portion 42 over the patient table 45 (FIG. 1).

The drape 10 extends between the upper front and rear free edges 34, 36 to respective front and rear lower edges 88, 90. The upper front and rear free edges 34, 36 are everted over an upper portion of the front and rear wall portions 22, 26 to provide an annular pocket 89 extending about the open upper end 38. The fasteners 40 are attached to an inner surface 91 of the rear and front wall portions 22, 26 and face radially inwardly toward the cavity 20. The fasteners 40 are configured to align for releasable attachment with the fasteners 82 of the radiation shield 12 adjacent the uppermost end 56 of the shield 12. Additional fasteners 92 are provided between the upper front and rear free edges 34, 36 and the front and rear lower edges 88, 90. The fasteners 92 are configured for releasable attachment to corresponding fasteners 40 on the radiation shield 12 to facilitate initial assembly, discussed further below.

The front and rear lower edges 88, 90 have an inverted substantially U-shaped openings 94 located centrally between the opposite side edges 30, 32 and aligned with one another to provide at least a portion of a fenestration 96 to register in with the fenestration 72 of the drape 12 in use. The openings 94 are preferably joined together, such as via a weld joint to provide a unitary opening 94. A fastener 98 is attached along an inner periphery of the opening 94 to facilitate attaching the periphery of the opening 94 in releasably fixed relation to the fastener 82 extending along the arcuate edge 78 of the radiation shield 12.

Figure 9:
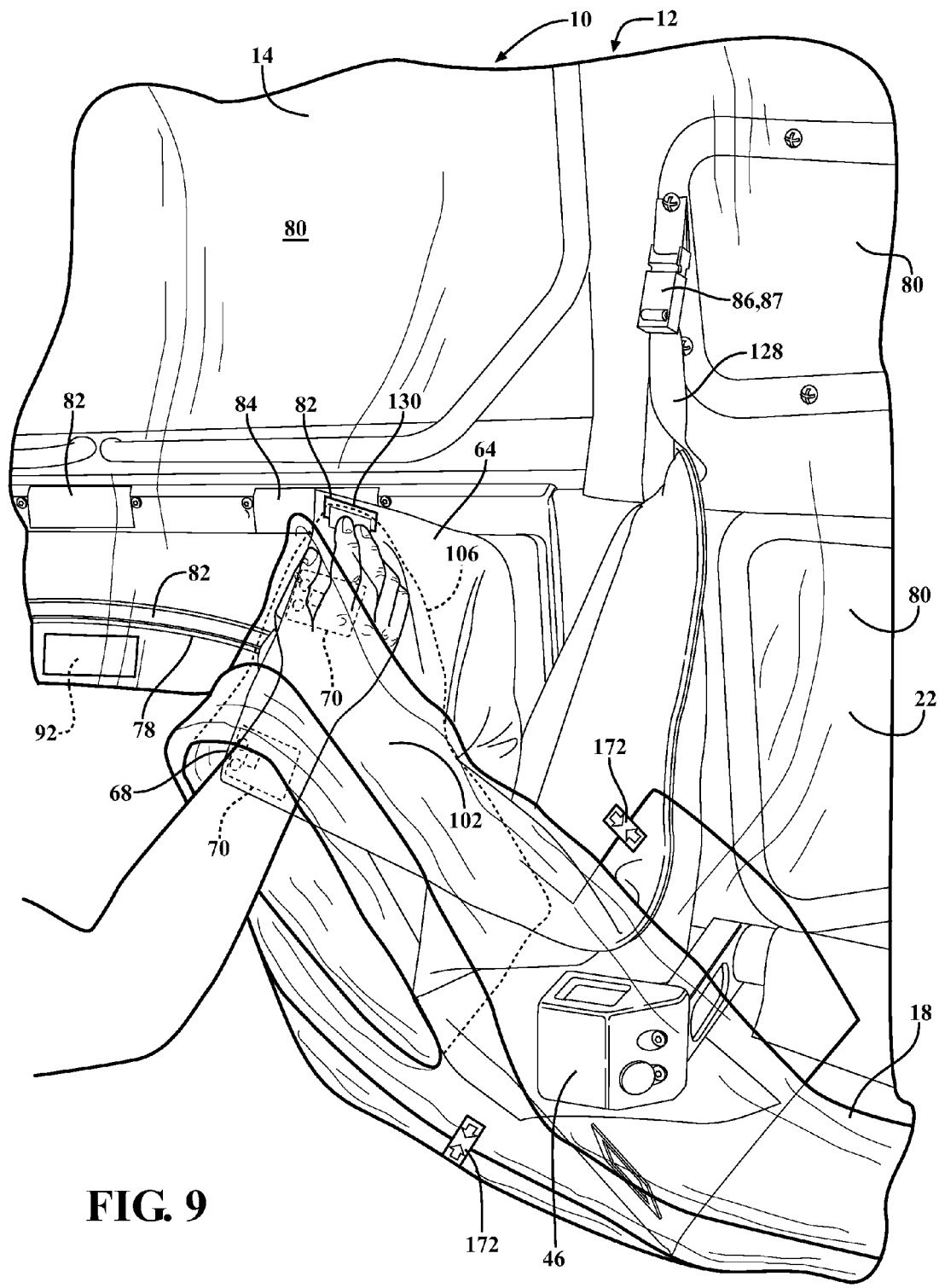
FIG. 9 illustrates a portion of a pocket of the disposable sterile drape being inverted and releasably attached to a portion of the radiation shield.
Figure 10:
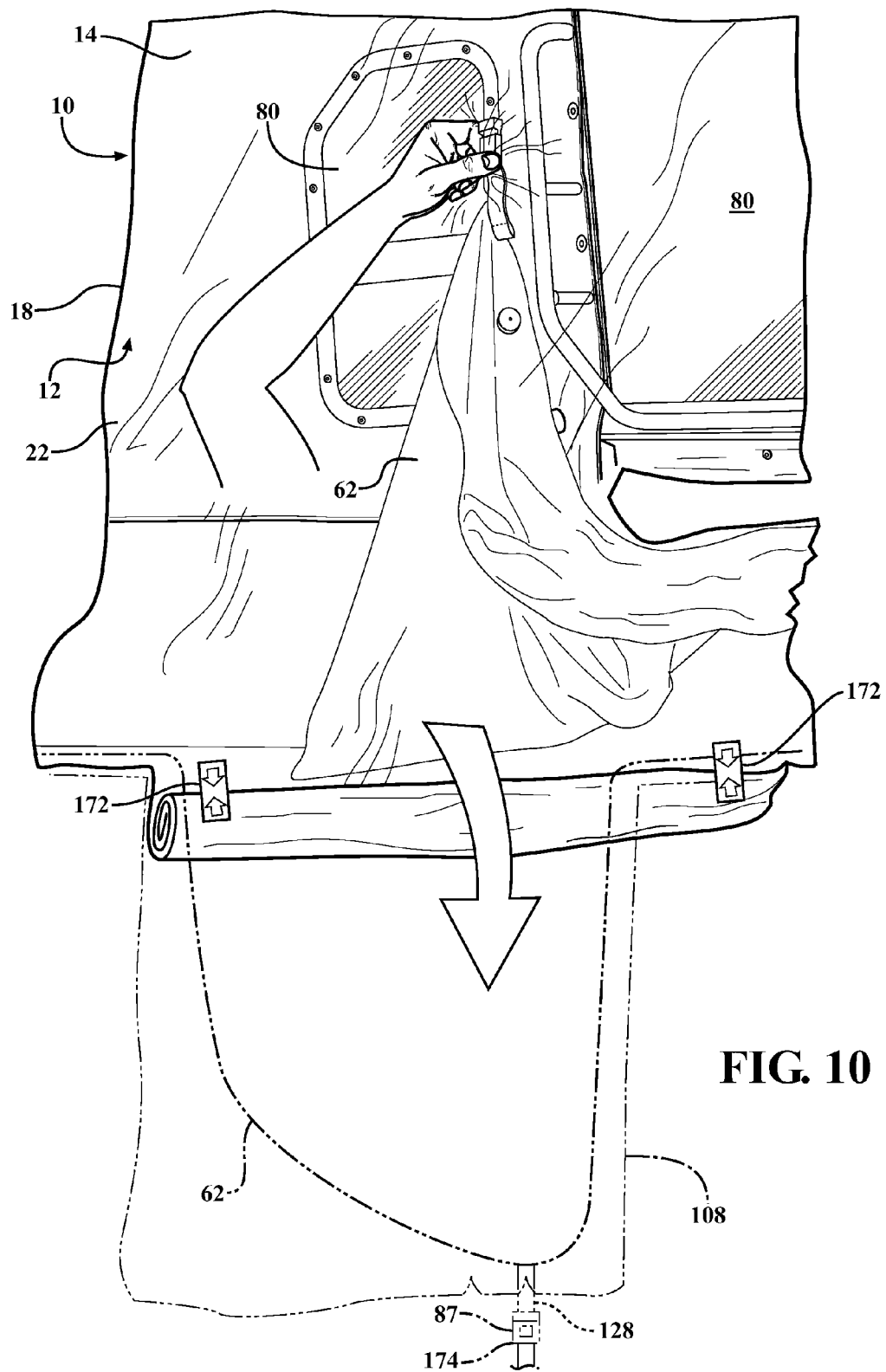
FIG. 10 illustrates the disposable sterile drape in a less than fully unfolded state in solid line with a portion of the radiation shield shown in solid line being released for receipt in an unfolded portion of the pocket shown in phantom line.

The front wall has a pair of pockets 100, 102 attached thereto for receipt of the radiation shield skirts 62, 64. The pockets 100, 102 are configured to cover and conform with the skirts 62, 64, and thus, are generally L-shaped in mirrored relation with one another across a midpoint of the drape 10. Each pocket 100, 102, being L-shaped, has horizontal legs 104, 106 and vertical legs 108, 110. The horizontal legs 104, 106 extend toward one another for overlapped mating with one another upon releasable securing the ends 66, 68 of the radiation skirts 62, 64 to one another in use. The horizontal legs 104, 106 have closed edges, with inner peripheral edges 109, 111 bounding a portion of the enclosed fenestration 96 in use. The vertical legs 108, 110 extend from open upper edges 112, 114 of the pockets 100, 102 downwardly beyond the horizontal legs 104, 106 along closed side edges 116, 118 to substantially closed bottom edges 120, 122. The substantially closed bottom edges 120, 122 have openings 124, 126 for receipt of fastener straps 128 of the fastener clips 87 of the radiation shield 12 therethrough during assembly, discussed further below. To facilitate disposing a portion of the radiation shield 12 in the horizontal legs 104, 106, as best shown in FIG. 9, each of the horizontal legs 104, 106 preferably has at least one fastener 130 located in a predetermined location internally therein, wherein at least one fastener 130 is preferably located in a far corner of the legs 104, 106 along the upper peripheral edges 108, 110, wherein the fasteners are configured for attachment to corresponding fasteners 82 on the radiation shield skirts 62, 64.

Figure 5:
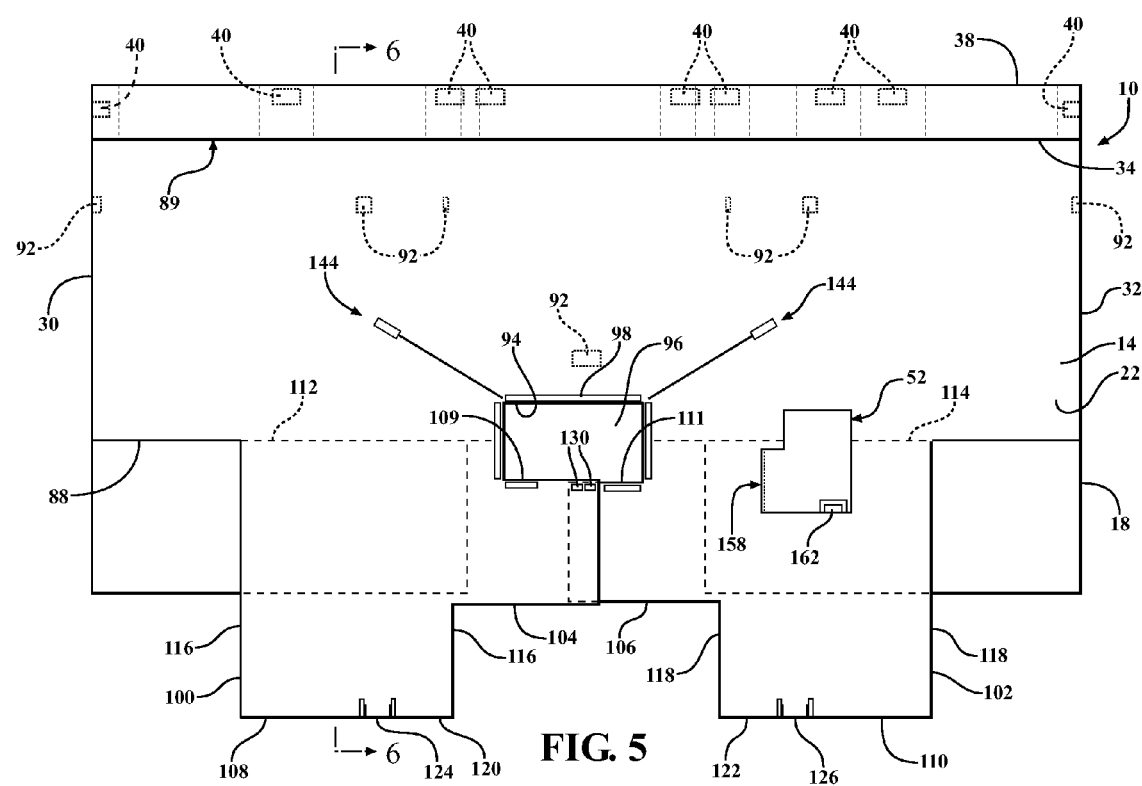
FIG. 5 illustrates a front plan view of the disposable sterile drape.
Figure 5A:
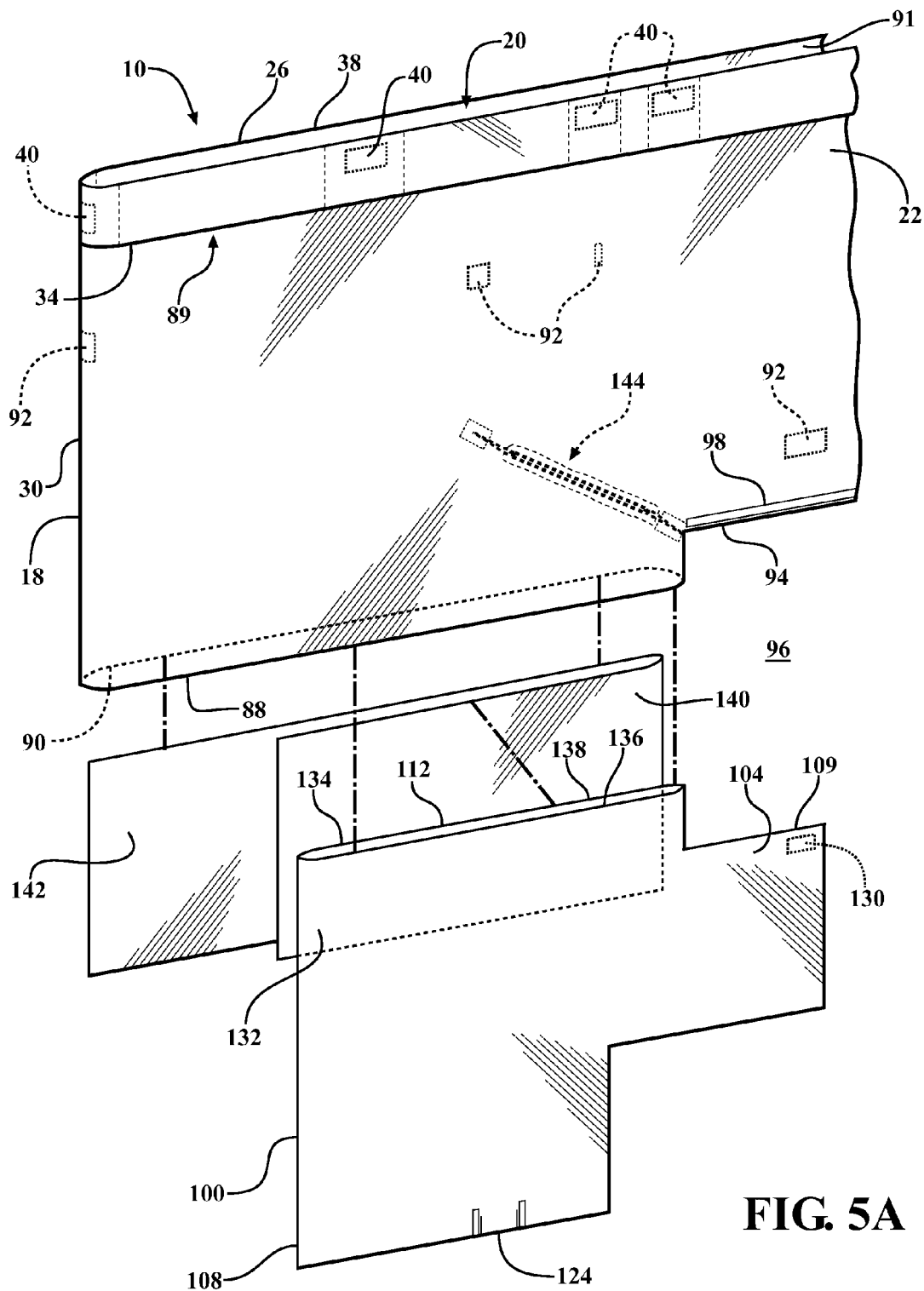
FIG. 5A illustrates a partial exploded view of the disposable sterile drape.

The construction of the pockets 100, 102 is shown in FIG. 5A. Each pocket 100, 102 has an outer wall 132 and an inner wall 134. The outer wall 132 has an upper edge portion 136 that is attached to the lower end 88 of the drape front wall portion 22 and an upper edge portion 138 that is attached to an intermediate wall 140 of a material, which remains free to provide the opening into the pockets 100, 102. The material of the intermediate wall 140 is reversed folded to provide a rear wall 142 that is attached to the lower end 90 of the drape rear wall portion 26.

Also shown clearly in FIG. 5A is a gathering feature 144 of the drape 10. The gathering feature 144 is provided to pull excess material forming the U-shaped opening 94 radially outwardly against the arcuate edge 78 of the radiation shield 12. As such, the fenestration 96 is formed without excess drape material obstructing the surgical team from utilizing the fenestrations 72, 96 as desired. The gathering feature 144 is provided in part by an elastic band 146 coupled at opposite ends 148, 150 to the rear wall portion 26 of the drape 10. The elastic band 146 is attached in a predetermined angular relation to the U-shaped opening 94, shown as extending slightly upwardly and outwardly therefrom, thereby pulling the excess material of the drape 10 in the desired direction against the radiation shield 12. To facilitate coupling the elastic band 146, a pair of string members 152 are adhered to the rear wall portion 26 via any suitable adhesive tape 154, or the like, wherein the string members 152 are then looped through the annular elastic band 146 and tied. To provide sterility about the elastic band 146, a conforming sleeve 156 of the drape material is disposed about the elastic band 146 prior to attaching the string members 152.

As best shown in FIGS. 11 and 12, the pouch 52 is generally L-shaped to receive and conform with the post 44 structure and receptacle 46 structure. The pouch 52 has an opening 158 along a portion that is attached to the front wall portion 22 of the drape 10 for close receipt of an arm 160 of the receptacle 46 therethrough. In addition, the pouch 52 has an another opening 162 sized for close receipt of the upstanding portion of the post 44 therethrough. The opening 162 is provided by a relatively rigid annular member 164, shown as being planar member, such as can be constructed from cardboard or plastic, by way of example and without limitation. The annular member 164 is attached to the plastic pouch 52 such that the sterile material of the pouch 52 covers the annular member 164. The opening 162 provided by the annular member 164 preferably conforms in shape to the cross-sectional shape of the post 44 to provide a close fit therewith. Other than the openings 158, 162, the pouch 52 is enclosed to shield the post 44 and receptacle 46 upon being disposed therein.

Figure 4:
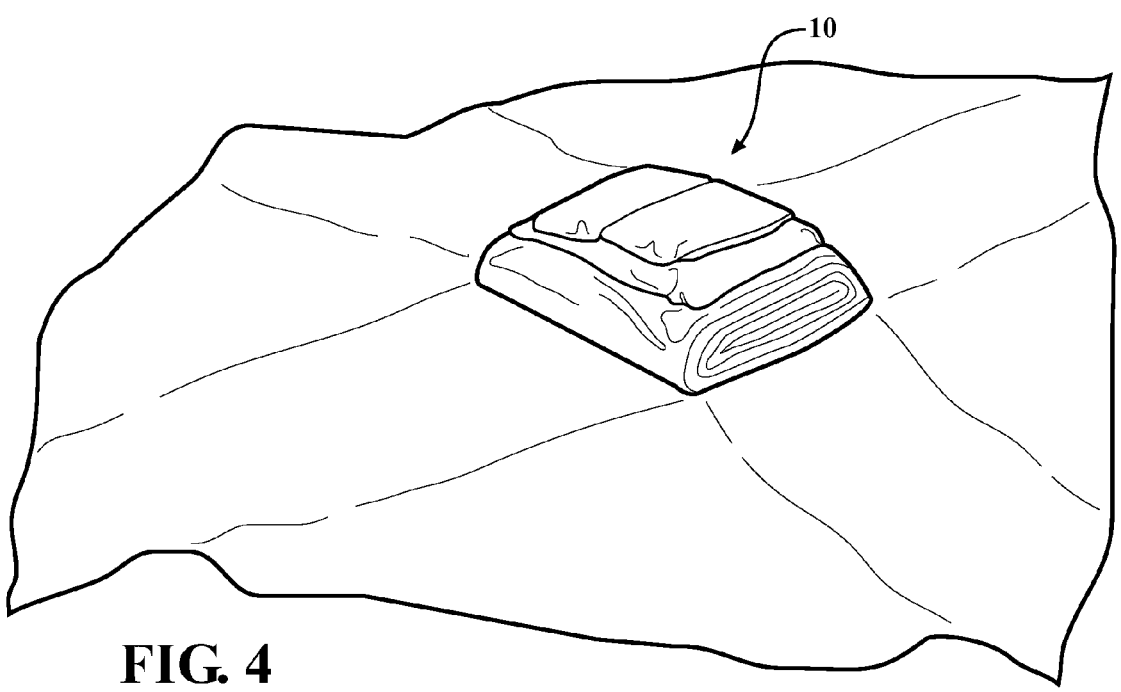
FIG. 4 illustrates the package of FIG. 3 opened with the disposable sterile drape in its predetermined folded state.

Up until the time of use, the drape 10 is maintained and stored in a sterile package 166. The package 166 has an upper layer 168 of polymeric material attached to a bottom layer 170 of polymeric material for selective detachment of the two layers 168, 170 from one another at the desired time of use. Accordingly, to release the drape 10 for use, the upper layer 168 is pealed from the bottom layer 170 to expose the sterile drape 10 (FIG. 4). Then, the drape 10, which is folded into a predetermine configuration with a plurality of adhesive tear tabs 172 releasably maintaining the drape 10 in its temporary, folded configuration and then rolled to its packaged configuration, is selectively unrolled to its full width, while still remaining folded via the un-torn tear tabs 172. When in its initially unrolled configuration, the front and rear free edges 34, 36 are exposed and positioned beneath the lowermost end 54 of the radiation shield 12. Then the front and rear free edges 34, 36 are lifted along the opposite sides 58, 60 of the radiation shield 12 as the drape 10 is selectively unfolded. As the strategically located tear tabs 172 become availed, they are selectively torn to allow the drape 10 to continue to be unfolded. By preventing the drape 10 from automatically unrolling in an uncontrolled manner via the tear tabs 172, the drape 10 can be readily maintained above the sterile height while assembling the drape 10 to the radiation shield 12, typically 34" in a surgical room. As the progression of installing the drape 10 continues, the fasteners 92 on the sides of the drape 10 are releasably attached to the fasteners 82 along the side of the radiation shield 12, and the central fastener 92 above the U-shaped opening 94 is attached to the corresponding fastener 82 above the arcuate edge 78. Then, the unfolding continues until the annular pocket 89 is exposed. Hands are inserted upwardly into the pocket 89 and the remaining fasteners 40 are releasably attached to the corresponding fasteners 82 adjacent the uppermost end 56 of the radiation shield 12. Then, the fastener 98 along the U-shaped opening 94 is attached to the fastener 82 extending along the arcuate edge 78.

Further, as shown in FIG. 9, a hand is inserted upwardly into each of the horizontal legs 104, 106 of the pockets 98, 100 to invert (turn inside out) the legs 104, 106 and to bring the fasteners 130 into attachment with corresponding fasteners 82 on the radiation shield skirts 62, 64. Upon attaching the respective fasteners 130, 82, portions of the skirts 62, 64 are pulled into the legs 104, 106 and then the fasteners 86, 87 are unclipped from one another to allow the remaining portions of the radiation shield skirts 62, 64 to fall into their respective pockets 100, 102.

Next, the radiation shield upper portion 16 is moved into its attached position with the lower portion 42, at which time the post 44 is disposed in the receptacle 46. Then, with the patient lying on the patient table 45, the ends 66, 68 of the skirts 62, 64 are brought into their overlapping relation with one another to complete formation of the fenestration 72, 96 whereupon the magnets 70 fasten to one another. At this time, the horizontal legs 104, 106 lie over the patient's legs or groin region, while the vertical legs 108, 110 hang freely downwardly on opposite sides of the patient table 45. To secure the vertical legs 108, 110 against any unwanted movement, the spring clips 87, being disposed through the openings 124, 126, can be clipped to mating spring clip receptacles 174 on the lower portion 42 (FIG. 1).

In addition, to further close off the fenestration 72 against any unwanted radiation flow through, a separate radiation shield and drape subassembly 176 can be disposed over the fenestration 72. The subassembly includes a generally U-shaped radiation shield 178 and a conforming drape 180 receiving the shield 178 therein. With the subassembly 176 being generally U-shaped, it can be reversed in use, thereby allowing a remaining portion of a reduced size fenestration 182 to be selectively provide on either side of the patient table 45. The drape 180 is enclosed, such as via a weld seam, along two sides 179 and one end 181, and open along one end 184 to allow the radiation shield 178 to be disposed in a cavity therein. Upon disposing the radiation shield 178 within the cavity, the end 182 can be folded over and fastened to close of the cavity, such as via self adhesive or hook and loop type fasteners, for example. Further, to facilitate maintaining the subassembly 176 is place over the larger fenestration 72, fasteners can be provide along both of the sides 179, such as self adhesive or hook and loop type fasteners, for example, for releasable attachment to a portion of the underlying drape 10. Further yet, to provide an absorbent periphery about the drape subassembly 176, an absorbent material 186 can be deployed between the drape subassembly 176 and the main drape 10.

Accordingly, the drapes 10, 180 provide an economical, quick and user friendly mechanism in which to provide a sterile surface about underlying radiation shielding 12, 178. The radiation shields 12, 178 and corresponding drapes 10, 180 allow the radiation emitting imaging equipment 79 to be used on the one side A of the drapes 12, 178, while the surgical team on the other side B is protected against unwanted exposure to the radiation, while further preserving the desired sterility of the underlying shield 12, 178 and overall sterility of the surgical theatre. Upon being used, the drapes 10, 180 can be readily disposed, being as they are constructed largely from plastic, wherein new drapes 10, 180 can be easily and quickly assembled about the leaded radiation shields 12, 178 for future use.

Figure 13:
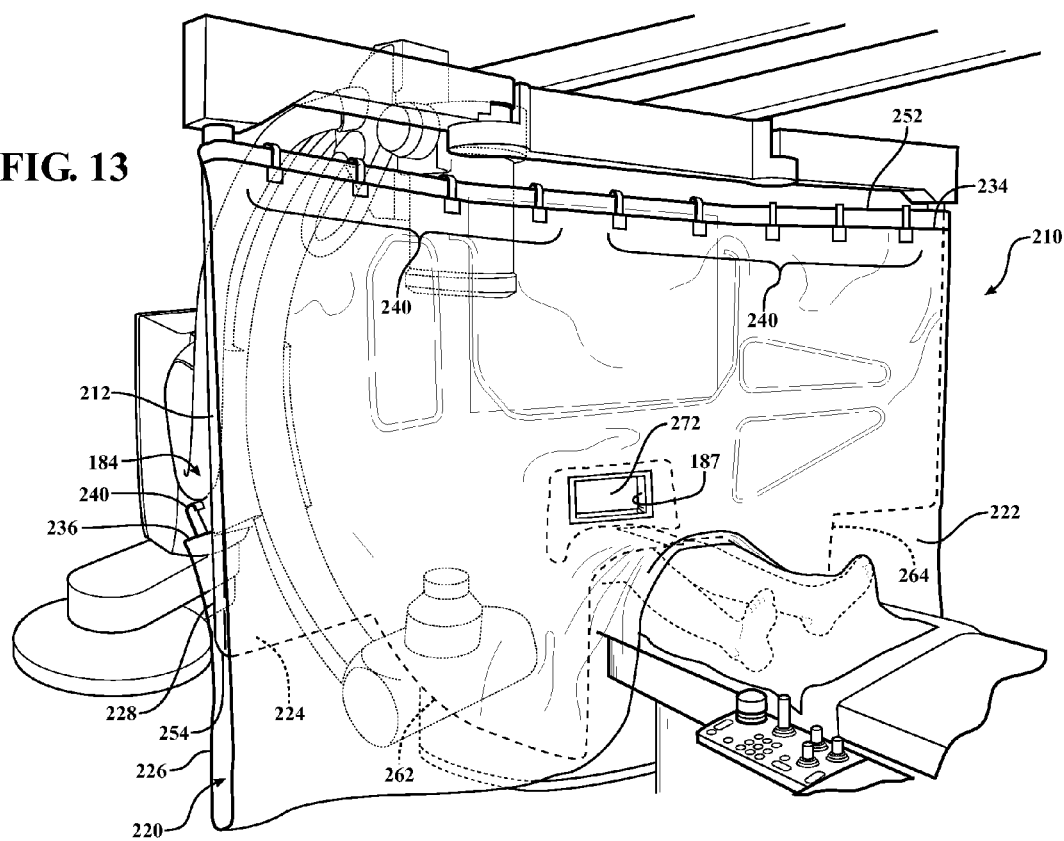
FIG. 13 illustrates a perspective front view of a disposable sterile drape disposed about a radiation shield in accordance with another aspect of the invention.

FIG. 13 shows a drape 210 constructed in accordance with another aspect of the invention, wherein the same reference numerals, offset by a factor of 200, are used to identify similar features.

The drape 210 is shown as being constructed from a single piece of typical drape material as discussed above, e.g., polyurethane film, polyethylene, polyvinylchloride, thermoplastic olefins, polypropylene, and copolymers of propylene and polyethylene. The drape 210 is initially formed as a generally flat piece extending between opposite front and rear free ends 234, 236. However, it is to be understood that multiple pieces of material could be used and bonded together to form the drape structure. To facilitate releasably fastening the front free end 234 to a radiation shield 212, a plurality of front fasteners 240 are attached to the front free end 234, wherein the front fasteners 240 are shown as being hooks configured to hang from an uppermost end 252 of the shield 212. To facilitate fastening the rear free end 236 to the radiation shield 212, a plurality of rear fasteners 240 are attached to the rear free end 236, wherein the rear fasteners 240 are shown as being hooks configured to hang from a centralized rear portion 184 of the shield 112. The drape 210 has a front wall portion 222 sized to extend along the full upstanding length of the radiation shield front portion 224 and a rear wall portion 226 sized to extend approximately mid-way up a rear portion 228.

During deployment, the front wall hooks 240 are first coupled to the uppermost end 252 of the shield 212 and then the drape 210 is reverse folded about the lowermost end 254 of the shield 212 to form a cavity 220 sized to receive at least in part the radiation shield 212 therein and to bring the rear wall hooks 240 into coupled orientation with a cross-member (not shown) on the rear portion 228 of the shield 212. The reverse fold is formed at a line 186 sufficiently low to allow skirts 262, 264 of the radiation shield 212 to fall as discussed above.

To provide a fenestration 272 through the drape 210, the front and rear wall portions 222, 226 have circumferentially enclosed openings 294 configured to align with one another upon reverse folding the drape 210. In addition, to provide a completely sealed passage through the aligned openings 294, a tubular member 187 is provided to extend from the front wall portion 222 through the rear wall portion 226. The tubular member 187 can be provided at least in part by a semi-rigid support 188 and at least in part by an overlying piece of drape material 190. Upon reverse folding the drape 212, the tubular member 187 extends completely between the openings 294, wherein the extended drape material 190 is brought into seal engagement with the adjoining drape material of the rear wall portion 226. It should be recognized that the tubular member 187 could be fixed to either, or both the front and rear wall portions 222, 226 to construct the seal through passage.

Obviously, many modifications and variations of the present invention are possible in light of the above teachings. It is, therefore, to be understood that within the scope of the appended claims, the invention may be practiced otherwise than as specifically described.

What is claimed is:

1. A surgical drape configured to provide a sterile outer surface on an upper portion of a suspended radiation shield, comprising:
    a flexible wall providing a cavity sized to receive the upper portion of the radiation shield therein, said wall having a rear wall portion configured to cover at least in part a rear portion of the radiation shield and a front wall portion configured to cover a front portion of the radiation shield, said front wall portion extending to an upper front free edge and said rear wall portion extending to an upper rear free edge, said upper front and rear free edges providing said wall with an open upper end;
    at least one fastener attached to at least one of said front and said rear wall portions adjacent respective ones of said upper front free edge and said rear free edge, said at least one fastener being configured to releasably fix said front and rear walls to said radiation shield;
    wherein said front wall portion includes a pair of pockets having open upper edges and closed lateral side edges, said pockets being configured for receipt of substantially conforming portions of the radiation shield.

2. The surgical drape of claim 1 wherein one of said lateral side edges of one of said pockets is configured for attachment to the other of said lateral side edges of the other of said pockets.

3. The surgical drape of claim 2 wherein said pair of pockets form at least in part a circumferentially enclosed fenestration extending through said front and rear wall portions.

4. The surgical drape of claim 3 further including at least one elastic member gathering material of said wall in a radially outwardly direction to prevent said material from hanging loosely in said fenestration.

5. The surgical drape of claim 1 further including at least one fastener inside each of said pair of pockets, said at least one fastener being configured for attachment to said portions of the radiation shield.

6. A surgical drape configured to provide a sterile outer surface on an upper portion of a suspended radiation shield, comprising:
    a flexible wall providing a cavity sized to receive the upper portion of the radiation shield therein, said wall having a rear wall portion configured to cover at least in part a rear portion of the radiation shield and a front wall portion configured to cover a front portion of the radiation shield, said front wall portion extending to an upper front free edge and said rear wall portion extending to an upper rear free edge, said upper front and rear free edges providing said wall with an open upper end;
    at least one fastener attached to at least one of said front and said rear wall portions adjacent respective ones of said upper front free edge and said rear free edge, said at least one fastener being configured to releasably fix said front and rear walls to said radiation shield; and
    wherein said front wall has front wall side edges with an opening located centrally between said front wall side edges and said rear wall has rear wall side edges with an opening located centrally between said rear wall side edges, said openings in said front wall and said rear wall being aligned with one another to provide at least in part a fenestration.

7. The surgical drape of claim 6 wherein said front wall includes a pair of pockets having open upper edges, closed laterally spaced side edges, said pockets being configured for receipt of portions of the radiation shield, wherein one of said laterally spaced side edges of one pocket is configured for attachment to another of said laterally spaced side edges of the other pocket.

8. The surgical drape of claim 7 wherein said pair of pockets form at least in part said fenestration.

9. The surgical drape of claim 8 further including at least one fastener adjacent said openings in said front wall, said at least one fastener being configured for attachment to the radiating shield.

10. A method of providing a sterile surface on a suspended radiation shield assembly, the radiation shield assembly having a radiation shield extending vertically between a laterally extending lowermost end and a laterally extending uppermost end, comprising:
    providing a folded, sterile flexible drape having a rear wall portion configured to cover at least in part a rear portion of the radiation shield and a front wall portion configured to cover a front portion of the radiation shield, the front wall portion extending to an upper front free edge and the rear wall portion extending to an upper rear free edge with at least one fastener attached adjacent to at least one of the front and rear free edges;
    positioning the lowermost edge of the radiation shield in a sterile region above a non-sterile field;
    joining the front and rear wall portions to one another along opposite side edges to form a tubular cavity sized to receive the radiation shield therein;
    positioning the flexible drape below the lowermost edge of the radiation shield within the sterile region and unfolding the drape upwardly along the radiation shield with the front wall portion on one side of the radiation shield and the rear wall portion on an opposite side of the radiation shield;

covering the front portion of the radiation shield with the front wall portion of the drape;
covering at least a portion of the rear portion of the radiation shield with the rear wall portion of the drape;
releasably attaching the flexible drape to the radiation shield at a plurality of locations while unfolding the drape; and
releasably attaching the upper front free edge and the upper rear free edge to the radiation shield assembly.

11. A method of providing a sterile surface on a suspended radiation shield assembly, the radiation shield assembly having a radiation shield extending vertically between a laterally extending lowermost end and a laterally extending uppermost end, comprising:
providing a folded, sterile flexible drape having a rear wall portion configured to cover at least in part a rear portion of the radiation shield and a front wall portion configured to cover a front portion of the radiation shield, the front wall portion extending to an upper front free edge and the rear wall portion extending to an upper rear free edge with at least one fastener attached adjacent to at least one of the front and rear free edges;
positioning the lowermost edge of the radiation shield in a sterile region above a non-sterile field;
joining the front and rear wall portions to one another along opposite side edges to form a tubular cavity sized to receive the radiation shield therein;
positioning the flexible drape below the lowermost edge of the radiation shield within the sterile region and unfolding the drape upwardly along the radiation shield with the front wall portion on one side of the radiation shield and the rear wall portion on an opposite side of the radiation shield;
covering the front portion of the radiation shield with the front wall portion of the drape;
covering at least a portion of the rear portion of the radiation shield with the rear wall portion of the drape;
releasably attaching the upper front free edge and the upper rear free edge to the radiation shield assembly;
folding the flexible drape into a predetermined configuration and attaching portions of the drape to one another with adhesive tabs prior to unfolding the drape.

12. The method of claim 11 further including tearing the adhesive tabs to allow the drape to extend downwardly along the full length of the radiation shield.

13. A method of providing a sterile surface on a suspended radiation shield assembly, the radiation shield assembly having a radiation shield extending vertically between a laterally extending lowermost end and a laterally extending uppermost end, comprising:
providing a folded, sterile flexible drape having a rear wall portion configured to cover at least in part a rear portion of the radiation shield and a front wall portion configured to cover a front portion of the radiation shield, the front wall portion extending to an upper front free edge and the rear wall portion extending to an upper rear free edge with at least one fastener attached adjacent to at least one of the front and rear free edges;
joining the front and rear wall portions to one another along opposite side edges to form a tubular cavity sized to receive the radiation shield therein;
positioning the lowermost edge of the radiation shield in a sterile region above a non-sterile field;
covering the front portion of the radiation shield with the front wall portion of the drape;
covering at least a portion of the rear portion of the radiation shield with the rear wall portion of the drape;
releasably attaching the upper front free edge and the upper rear free edge to the radiation shield assembly;
providing the front wall portion with a pair of pockets having open upper edges and closed lateral side edges with each of the pockets being configured for receipt of substantially conforming portions of the radiation shield.

14. The method of claim 13 further including providing at least one fastener inside each of said pockets and attaching the at least one fasteners to portions of the radiation shield.

15. The method of claim 14 further including inverting the pockets to attach the at least one fasteners to the radiation shield.

16. The method of claim 13 further including attaching one of the lateral side edges of one pocket to the another lateral side edge of the other pocket to form a circumferentially enclosed fenestration through the front and rear wall portions.

17. The method of claim 16 further including pulling material of the drape radially outwardly from the fenestration with elastic members attached to the drape.

18. The method of claim 16 further including disposing a separate radiation shield and drape subassembly over the fenestration to at least partially cover the fenestration.

19. A method of providing a sterile surface on a suspended radiation shield assembly, the radiation shield assembly having a radiation shield extending vertically between a laterally extending lowermost end and a laterally extending uppermost end, comprising:
providing a folded, sterile flexible drape having a rear wall portion configured to cover at least in part a rear portion of the radiation shield and a front wall portion configured to cover a front portion of the radiation shield, the front wall portion extending to an upper front free edge and the rear wall portion extending to an upper rear free edge with at least one fastener attached adjacent to at least one of the front and rear free edges;
positioning the lowermost edge of the radiation shield in a sterile region above a non-sterile field;
covering the front portion of the radiation shield with the front wall portion of the drape;
covering at least a portion of the rear portion of the radiation shield with the rear wall portion of the drape;
releasably attaching the upper front free edge and the upper rear free edge to the radiation shield assembly; and
providing an opening in each of the front wall portion and the rear wall portion and bring the openings into alignment with one another.

20. The method of claim 19 further including extending a tubular member between the aligned openings.

* * * * *